US005661123A

United States Patent [19]
Stalker et al.

[11] Patent Number: 5,661,123
[45] Date of Patent: Aug. 26, 1997

[54] ENTERAL COMPOSITION FOR MALABSORBING PATIENTS

[75] Inventors: Lance Stalker, Grayslake; Diana Twyman, Chicago; Shen-Youn Chang, Wadsworth, all of Ill.; Veronique Jaussan, Caen, France

[73] Assignee: Nestec, Ltd., Vevey, Switzerland

[21] Appl. No.: 372,980

[22] Filed: Jan. 17, 1995

[51] Int. Cl.$^6$ .......................... A61K 38/01; A61K 31/70; A61K 31/225; A61K 31/20; A61K 31/12; A61K 31/14; A61K 31/34; A61K 31/11; A61K 31/185; A61K 31/205; A61K 31/015

[52] U.S. Cl. .................. 514/2; 514/23; 514/547; 514/560; 514/681; 514/643; 514/474; 514/702; 514/578; 514/556; 514/763

[58] Field of Search ................... 514/2, 23, 547, 514/560, 474, 578, 556, 763; 424/681, 643, 702

[56] References Cited

U.S. PATENT DOCUMENTS 5,422,127   6/1995   Dube et al. ........................ 426/73

OTHER PUBLICATIONS

Silk DBA. Nutritional Support in Hospital Practice, Oxford, Scientific Publications, 1983; 80-81.
Mahan LK, Arlin M. Nutritional care in intestinal disease. In Mahan LK, Arlin M. Krause's Food, Nutrition and Diet Therapy. Philadelphia, PA. WB Saunders. 1992.
Spiller RC, Silk DB. Malabsorbtion, In Nutrition and Metabolism in Patient Care. Kinney JM, Jeejeebhoy KN, Hill GL, Owen OE, eds. Philadelphia, PA. WB Saunders, 1988; 281–304.
Zaloga GP, Studies comparing intact protein, peptide, and amino acid formulas. In Bounous G. ed. Elemental Diets in Clinical Situations, Boca Raton, FL. CRC Press; 1993, pp. 201–217.
Ortia C. Candau P. Arock M, et al. A comparative post–operative study—an enteral solution based on free amino acids, Gastroenterologic Clinique et Biologique. 1985;9:182–183.
Granger CN, Brinson, RR. Intestinal absorption of elemental and standard enteral formulas in hypoproteinemic (volume expanded) rats. J Parenter Enteral Nutr. 1988;12:278–281.
Brinson Rr, Curtis WD, Singh M. The role of hypoalbuminemia and the response to a chemically–defined diet (case reports and review of literature). J Am Coll Nutr. 1987;517–523.
Bounous G, Le Bel E. Shuster J. et al. Dietary protection during radiation therapy. Strahlentherapie. 1975;149;476–483.
Brinson RR, Pitts VL, Taylor AE. Intestinal absorption of peptide enteral formulas in hypoproteinemic (volume expanded) rats: a paired analysis. Crit Care med. 1989; 17:647–660.
Ziegler F. et al., Fluid Intake, renal solute load, and water balance in infancy. Journ. Pediatrics, Apr. 1971, vol. 78, pp. 561–568.
Brinson RR Kolts BE. Diarrhea associated with severe hypoalbuminemia: a comparison of peptide–based chemically defined diet and standard enteral alimentation. Crit Care Med. 1988:16:130–136.
Meredith JW, Ditesheim JA, Zaloga GP. Visceral protein levels in trauma patients are greater with peptide diet than intact protein diet. J. Trauma. 1990:30:825–829.
Shou J. Ruelaz E.A, Redmond HP, et al. Dietary protein prevents bacterial translocation from the gut. J Parenter Enteral Nutr. 1991:15(suppl); 29. Abstract.
Zaloga GP. Ward K.A, Prielipp RC. Effect of enteral diets on whole body and gut growth in unstressed rats. J Parenter Enteral Nutr. 1991:15:42–47.
Janne P. Carpentier Y. Willems G. Colonic Mucosal atrophy induced by a liquid elemental diet in rats. Dig Dis Sci. 1977:22:808–812.
Birke H. Thoiacus–Ussing O. Hessov I. Trophic effect of dietary peptides on mucosa in the rat bowel. J. Parenter Enteral Nutr. 1990:14(suppl):26. Abstract.
Jahoor F. Desai M. Herndon DN, Wolfe RR. Dynamics of the protein metabolic response to burn injury. Metab Clin. Exp. 1988:4:330–337.
Smith JL, Artega C. Heymsfield SB. Increased ureagenesis and impaired nitrogen use during infusion of a synthetic amino acid formula. N Engl J Med. 1982:306:1013–1018.
Brinson RR. The effect of peptide–based diet on the intestinal microcirculation in a rat model. Nutr Clin. Prac. 1990:238–240.
Zaloga GP, Meredith JS, et al. Improved hepatic protein responses with hydrolyzed protein versus intact protein diets after trauma. Crit Care Med. 1992:20 (suppl): 94.Abstract.
Zaloga GP, Knowles R. Black K. et al. Total parenteral nutrition increases mortality after hemorrhage. Crit Care Med. 1991:19:54–59.
Poullain MG, Cezard JP, Roger L. et al. Effects of whey proteins their oligopeptide hydrolysates and free amino acid mixtures on growth and nitrogen retention in fed and starved rats. J Parenter Enteral Nutr. 1989:13:382–386.

(List continued on next page.)

*Primary Examiner*—William R. A. Jarvis
*Attorney, Agent, or Firm*—Hill, Steadman & Simpson

[57]  ABSTRACT

The present invention provides a method for providing nutrition to non-catabolic and moderately catabolic patients. Pursuant to the present invention, the enteral composition includes a peptide based protein source of hydrolyzed whey, a lipid source, and a carbohydrate source. Preferably, the protein source includes approximately 22% to about 27% of the total calories. The composition has a caloric density of approximately 1000 Kcal/L and a low osmolality of approximately 300 to 450 mOsm/Kg $H_2O$. Still further, the composition of the present invention also includes increased levels of certain vitamins and minerals.

36 Claims, No Drawings

OTHER PUBLICATIONS

Mandt JM. Teasley–Strausberg KM, Shronts ED. Nutritional requirements. In Teasley–Strausberg (ed). Nutritional Support Handbook. Cincinnati, OH. Howard Whitney Books Co. 1992, pp.19–36.

Long CL. Schaffel N. Gieger JW, et al. Metabolic response to injury and illness; estimation of energy and protein needs from indirect calorimetry and nitrogen balance. J Parenter Enteral Nutr. 1979:3:452–455.

Kisseleff HR. Van Itallie RB. Physiology of the control of food intake. Ann Rev Nutr. 1982:2:371–418.

Stotts N. Washington D. Nutrition: a critical component of wound healing. AACN Clin Issues. 1990:1:585–594.

Chwals WJ, Infant and pediatric nutrition. In Zaloga G. (ed). Nutrition in Critical Care. Mosby. St Louis. 1994, pp. 727–763.

Law DK, Dudrick SJ, Abdou NI. The effect of dietary protein depletion on immunocompetence. Ann Surg. 1974:179:168–173.

Dominioni L. Trocki O, Fang CH. et al. Enteral feeding in burn hypermetabolism: nutritional and metabolic effects of different levels of calories and protein intake. J. Parenter Enteral Nutr. 1985:9:269–279.

Dominioni L. Trocki O, Mochizuki H. e al. Prevention of severe postburn hypermetabolism and catabolism by immediate intragastric feeding. J Burn Care Rehab. 1984:5:106–112.

Chernoff R.S. Milton K.Y. Lipshitz DA. The effect of a very high–protein liquid formula (Replete) on decubitus ulcer healing in long–term tube–fed institutionalized patients. J Am Diet Assoc. 1991:90:A130.

Breslow R. Hallfrisch J. Gut DG. et al. The importance of dietary protein in healing pressure ulcers. J. Am Geriatr Soc. 1993:41:357–362.

Breslow R. Nutritional status and dietary intake of patients with pressure ulcers; a review of research literature 1943–1989. Decubitus. 1991:4:16–21.

Twyman DL, Young AB, Ott L. et al. High protein enteral feedings; a means of achieving positive nitrogen balance in head–injured patients. J Parenter Enteral Nutr. 1985:9:679–684.

Young BY, Ott L. Norton J. et al. Metabolic and nutritional sequela in the non–steroid treated head–injured patient. Neurosurgery. 1985:17:784–791.

Matsuda T. Cagen RJ, Hanumadass M. Jonasson O. beneficial effects of aggressive protein feeding in severely burned children. Ann Sugg. 1980:192:505–517.

Cerra FB, Shronts EP. Raup S. et al. Enteral nutrition in hypermetabolic surgical patients. Crit Care Med. 1989:17:619–622.

Cerra FB, Blackburn G. Hirsh J. et al. Effects of stress level, amino acid formula, and nitrogen dose on nitrogen retention in traumatic and septic stress. Surgery. 1987:205; pp. 282–287.

Ireton–Jones CS, Baxter CR. Nutrition for adult burn patients: a review. Nutr. Clin prac. 1991:6:3–7.

Waxman K. Rebello T, Pinderski L. et al. Protein Loss Across Burn Wounds. J. Trauma. 1987:27:136–140.

Belcher HJ. Desai M. Herndon DN. Wolfe RD. Determinants of urinary nitrogen excretion in burned patients. Burns 1988:14:303–307.

Jahoor F., Desai M., Herndon DN., Wolfe R. Dynamics of the protein metabolic response to burn injury. Metab. Clin. Exp. 1988:4:330–337.

Alexander W., Macmillan BG, Stinnett J. et al. Beneficial effects of aggressive protein feeding in severely burned children. Ann Surg. 1980:192:505–517.

Fabiani C., Candy S., Oral hyperalimentation in the nutritional management of burned patients. So Afr Med J. 1985:67:768–770.

Clifton GL, Robertson CK, Grossman R.G. et al. The metabolic response to severe head injury. J. Neurosurg. 1984:60:687–696.

Annis K., Ott L., Kearney PA. Nutritional support of the severe head–injured patient. Nutr. Clin Prac. 1991:6:245–250.

Chioler R., Schuz Y., Lemarchand TH, et al. Hormonal and metabolic changes following severe head injury or noncranial injury. J Parenter Enteral Nutr. 1989:13:5–12.

Cerra FB, Bankey PE, Maziski JE, Negro F. What's new in nutrition support in critical care? In Kinney JM, Borum PR (eds). Perspectives in Clinical Nutrition. Baltimore–Munich: Urban and Schwartzenberg: 1989, pp. 323–338.

Bynoe RP, Kudsk K.A. Fabian TC, Brown RO. Nutrition support in trauma patients. Nutr Clin Prac. 1988:4:137–144.

McClave SA, Lowen CC, Snider HL, Immunonutrition and enteral hyperalimentation of critically ill patients. Dig. Dis. Sci. 1992:37:1153–1161.

Cerra FB, Shronts EP, Raup S, et al. Enteral nutrition in hypermetabolic surgical patients. Crit Care Med. 1989:17:619–622.

Jeppeson M. Laboratory values for the elderly. In Carnevalli DL (ed). Nursing Management of the Elderly. Philadelphia, PA. Lippencott. 1986, pp. 102–142.

Gardner BC. Guide to changing lab values in elders. Geriatric Nursing. 1989: May/Jun.: 144–145.

Brinson R.R. Pitts VL, Taylor AE. Intestinal absorption of peptide enteral formulas in hypoproteinemic (volume expanded) rats; a paired analysis, Crit Care Med. 1989:17:647–660.

Borlase BD, Bell SJ. Lewis EJ. et al. Tolerance to enteral tube feeding diets in hypoalbuminemia critically ill geriatric patient. Surg. Gynecol. Obstet. 1992:174:181–188.

Trocki O. Mochizuki H. Dominioni L. et al. Intact protein versus free amino acids in the nutritional support of thermally–injured animals. J Parenter Enteral Nutr. 1986:10:139–145.

Ziegler F. Olliver JM. Cynobar L. et al. Efficacy of enteral nitrogen support in surgical patients; small peptides vs. non–degraded proteins. Gut. 1990:31:1277–1283.

Brinson RR Kolts BE, Diarrhea associated with severe hypoalbuminemia: a comparison of peptide–based chemically defined diet and standard enteral alimentation. Crit Care Med. 1988:16:130–136.

Brinson Rr. Curtis WD, Singh M. Diarrhea in the intensive care unit; the role of hypoalbuminemia and the response to a chemically defined diet (case reports and a review of the literature) J Am Coll nutr. 1987:6:517–523.

Meredith JW. Ditesheim JA, Zaloga GP, Visceral protein levels in trauma patients are greater with peptide diet than intact protein diet. J Trauma. 1990:30:825–829.

Steinhardt HJ. Wolf A. Jakober B. et al. Nitrogen absorption in pancreatomized patients; protein versus protein hydrolysate as substrate. J Lab Clin Med. 1989:113:162–167.

Curtis KJ. Gainers HD, Kim YS. Protein digestion and absorption in rats with pancreatic duct occlusion. Gastroenterology. 1979:74:1271–1276.

Milla PJ Kilby A. Rassam UB, Esser R. Harries JT. Small intestinal absorption of amino acids and a dipeptide in pancreatic insufficiency. Gut. 1983:24–818–824.

Smith JL, Argega C. Heymsfield SB. Increased ureagenesis and impaired nitrogen use during infusion of a synthetic amino acid formula. N Engl J Med. 1982:306:1013–1018.

Vanderhoff JA. Evaluation of a fat containing elemental diet for treatment of short bowel syndrome in children. J Parenter Enteral Nutr. 1982:12(suppl): 21. Abstract.

Cosnes J. Evard D. Beaugerie L. Gendre JP. Le Quintrec L. Improvement in protein absorption with a small peptide–based diet in patients with high output jejunostomy. Nutrition. 1992:8:406–411.

Voss T. Rowe B. Graf L. Keyes C. Beal J. Management of HIV related weight loss and diarrhea with an enteral formula containing whey peptides and medium–chain triglycerides. 7th International Conf. on AIDS. Jun. 16–21, 1991:7:223. Abstract.

Beer WH, Fan A. Halsted CH. Clinical and nutritional implications of radiation enteritis. Am J Clin Nutr. 1985. 1985:41:85–91.

Brinson RR. The effect of peptide–based diets on the microcirculation in a rat model. Nutr Clin Prac. 1990:5:238–240.

Zaloga GP, Ward KA, Prielipp RC. Effect of enteral diets on whole body and gut growth in unstressed rats. J Parenter Enteral Nutr. 1991:15:42–47.

Shou J. Ruelaz EA, Redmond HP. et al. Dietary protein prevents bacterial translocation from the gut. J Parenter Enteral Nutr. 1991:15(suppl):29. Abstract.

Janne P. Carpentier Y, Willems G. Colonic Muscosal atrophy induced by a liquid elemental diet in rats. Dig Dis Sci. 1977:22:808–812.

Morin CL, Ling V. Bourassa D. Small intestinal and colonic changes induced by a chemically–defined diet. Dig Dis Sci. 1980:25:123–128.

Shou J. Minnard E. Motyka L. Daly JM. Interleukin–4 reduces chemically–defined diet (CDD) induced bacterial translocation in mice. J Parenter Enteral Nutr. 1992:16:(suppl):24. Abstract.

Bounous G. Sutherland NG. McArdle AH, Gurd FN. The prophylactic use of an "elemental" diet in experimental hemorrhagic and intestinal shock and in intestinal ischemia. Ann Surg. 1967:166:312:343.

Anderson W. Brinson RR. Conrad SA, Robinson RH. Intestinal protein loss during enteral alimentation in critically ill patient. J Parenter Enteral nutr. 1990:14(suppl):24. Abstract.

Joint FAO/WHO ad hoc expert committee. Energy and protein requirements. World Health Organization technical report series No. 522. Geneva: World Health organization, 1973.

Rose WC. The nutritive significance of the amino acids and certain related compounds. Science. 1937:86:298–300.

Charney RJ. Arginine, Nutrition Support Line 1994:16:15–17.

Visek WJ. Arginine needs, physiological state and usual diets: a reevaluation. J. Nutr. 1986:116:36–46.

Souba SS, Klimberg VS Hautamaki RD, et al. Oral glutamine reduces bacterial translocation following abdominal radiation. J Surg. Res. 1990:48:1–5.

Fox AD, DePaula JA. Krinke SA, et al. Glutamine–supplemented enteral diets reduce endotoxemia in a lethal model of enterocolitis. Surg Forum. 1988:39:46–48.

Fox AD Kripke SA, DePaula J, et al. Effect of a glutamine–supplemented enteral diet on methotrexate induced enterocolitis. J Parenter Enteral Nutr. 1988:12:325–331.

D'Attellis N. Skeie B, Kvetan V. Branched–chain amino acids. In Zaloga G. (ed). Nutrition in Critical Illness. St. Louis, MO. Mosby:1994, pp. 81–106.

Heymsfield SB, Head SA, McManus CB, et al. Respiratory, cardiovascular, and metabolic effects of enteral hyperalimentation; influence of formula dose and composition. Am J Clin Nutr 1984:40:116–30.

Bell SJ. Mascioli EA, Bistrian B, Babyan VK, Blackburn GL, et al. Alternative lipid sources for enteral and parenteral nutrition: Long–and medium–chain triglycerides, structured triglycerides, and fish oils. J Am Diet Assoc. 1991:91:74–78.

Olley PM, Coceani F. The prostaglandins. Am J Disc Child. 1980:134:688–696.

Friedman Z. Essential fatty acids revisted. Am J Dis Child. 1980:134:397–408.

Bach A. Babyan VK. Medium–chain triglycerides: an update. am J Clin Nutr. 1982:36:950–962.

Johnson RC, Cotter R. Metabolism of medium–chain triglycerides lipid emulsion. Nutr. Intl. 1986:2:150–158.

Cahill GF. Ketosis. J Parenter Enteral Nutr. 1981:5:281–287.

Holt PR. Medium chain triglycerides. A useful adjunct in nutritional therapy. Gastroenterology. 1967:53:961–966.

Greenberger NJ Summerskill TG. Medium–chain triglycerides–physiologic considerations and clinical implications. N Engl J Med. 1969:280:1045–1058.

Sailer D. Muller M. Medium chain triglycerides in parenteral nutrition. J Parenter Enteral Nutr. 1981:5:115–119.

Randall S. Mascioli E. Bistrian B. et al. Randomized clinical trial in hospitalized patients using intravenous medium chain triglyceride emulsions. Clin Res. 1985:33:276, Abstract.

Mascioli E. Diamondis, CP et al. Intravenous administration of mixture of medium and long–chain triglyderide emulsion. Clin. Res. 1985:33:275, Abstract.

Sucher KP. Medium chain triglycerides: a review of therapeutic enteral use in clinical nutrition. Nutr. Clin Prac. 1986:146–150.

Holman RT. Function and biological activities of essential fatty acids in man. In Meng HC, Wilmore DW. (eds). Fat Emulsion in Parenteral Nutrition. Chicago: American Medical Association. 1976:5–14.

Bjerve KS, Fischer S, Alme K. Alpha–linolenic acid deficiency in man: effect of ethyl linolenate on plasma and erythrocyte fatty acid composition and biosynthesis on prostanoids. Am J Clin Nutr. 1987:46:570–576.

Bjerve KS, Mostad I. Thoreson L. Alpha–linolenic acid deficiency in patients on long term gastric tube–feeding: estimation of linolenic acid and long–chain unsaturated n–3 fatty acid requirement in man. Am J Clin Nutr. 1987:45:66–77.

Simopoulos AP. Executive summary. In Dietary Omega–3 and Omega–6. Biological effects and nutritional essentiality. Galli C. Simoupoulos AP. (eds) ASI Series A, Life Sciences. 1988, pp. 391–402.

Simoupoulos AP. Omega–3 fatty acids in health and disease and in growth and development. Am J Clin Nutr. 1991:54:438–63.

Kafatos A. Comas G. Biological effects of olive oil on human health. In Kafatos A. (ed.). Olive Oil. AOCS. 1990, pp. 157–181.

Leyton J. Drury PJ. Crawford M. Differential oxidation of saturated and unsaturated fatty acids in vitro in the rat. Br J Nutr. 1987:383–393.

Anonymous. Inhibition of lipid peroxidation by monounsaturated fatty acids. Nutr Rev. 1989:47:126–128.

Bach AC, Babyan VK, Medium–chain triglycerides: an update. Am J Clin Nutr. 1982:36:950–962.

Kaunitz H. Clinical uses of medium–chain triglycerides. Drug Therapy. 1978:8:91–96.

Gray GM. assimilation of dietary carbohydrates. In Shils M. (ed) Defined formula diet for medical purposes. Chicago: American Medical Association, 1977:24–28.

Scrimshaw NS, Murray EB. The acceptability of milk and milk products populations with a high prevalence of lactose intolerance. Amer J. Clin Nutr. 1988:48:1082–1159.

Gottschlich M. Alexander JW Bower R. Enteral nutrition in patients with burns or trauma. In Rombeau JL, Caldwell MD (eds) Enteral and Tube Feeding, Philadelphia, PA: WB Saunders Co: 1990, pp. 306–324.

Gann DS, Robinson HB. Salt, water and vitamins. In Ballinger WF, Collins JA, Drucker WR, Dudrick SJ, Zeppa R. (eds.) Manual of surgical nutrition. Philadelphia: WB Saunders 1975, pp. 73–90.

Goldsmith FA. Curative nutrition: vitamins. In: Schneider HA, Anderson CE, Coursin DB, (eds.) Nutritional support of medical practice. Hagerstown, MD. Harper and Row, 1977:101–123.

Lemoine A, Le Devehat C. Codaccioni JL, Monges A. et al. Vitamin B1, B2, B6 and C status in hospital inpatients. Am J Clin Nutr. 1980:33:2595–2600.

Goodson WH, Hunt TK. Wound healing. In: Kinney J. Jeejeebhoy K, Hill G. Owen O. (eds.). Nutrition and Metabolism in Patient Care. Philadelphia, PA: WB Saunders, 1988, pp. 635–641.

Ross R, Benditt EP: Wound healing and collagen formation. II. Fine structure in experimental scurvy. J Cell Biol. 1962:12:533–551.

Ross R. Benditt EP: Wound healing and collagen formation. V. Quantitive electron microscope radioautographic observations of proline–$H^3$ utilization by fibroblasts. J Cell Biol. 1965:27:83–106.

England S, Seifter E: The biochemical functions of ascorbic acid. Ann Rev Nutr. 1986:6:365–406.

Chojkier M. Spanheimer R. Peterkofsky B: Specifically decreased collagen biosynthesis in scurvy dissociated from an effect on proline hydroxylation and correlated with body weight loss. In vitro studies in 2guinea pig calvarial bones. J Clin Invest. 1983:72:825–835.

Schwartz RI, Mandell RB, Bissell MJ: ascorbate induction of collagen synthesis as a means for elucidating mechanism for quanitive control of tissue–specific function. Mol Cell Biol. 1981:1:843–153.

Robertson WV, Schwartz B: Ascorbic acid and formation of collagen. J. Biol. Chem. 1953:201:689–696.

Stotts N, Washington D. nutrition: a critical component of wound healing. AACN Clin Issues. 1990:1:585–594.

Irvin TT, Chattopadhay DK, Smythe A. Ascorbic acid requirements in post–operative patients. Surg. Gynecol. Obstet. 1978:147:49–55.

Ringsdorf WM, Cheraskin E. Vitamin C and human wound healing. Oral Surg. 1982:53:231–236.

Hadley SA, Fitzsimmons L. Nutrition in wound healing. Top Clin Nutr. 1990:5:72–81.

Levenson S. Seifter E. Van Winkle W. Nutrition. In Hunt TK (ed.). Fundamentals of Wound Management. New York, NY. Appleton–Century Crofts. 1979.

Levenson S. Micronutrients (vitamins and trace minerals). In ASPEN program manuel of proceedings of the 16th Clinical Congress. 1922:189–198.

Gottschlich M. Warden G. Vitamin supplementation in the patient with burns. J. Burn Care Rehab. 1990:11:275–279.

Erlich H. Tarver H. Effects of beta carotene, vitamin A. and glucocorticoids on collagen, synthesis in wounds. Proc. Soc. Exp Biol Med. 1971:137:936–938.

Szbeni A. Negyesi G. Feuer L. Vitamin A levels in serum of burned patients. Burns 1981:7:313–318.

Ehrlich HP, Hunt TK. Effects of cortisone and vitamin A on wound healing. Ann Surg.1968:167:324–328.

Ehrlich HP, Tarvet H. Hunt TK, Effects of vitamin A and glucocorticoids upon inflammation and collagen synthesis. Ann Surg. 1973:177:22–227.

Hunt TK. Control of wound healing and cortisone and vitamin A. In Longacre JJ (ed.) The Ultrastructure of Collagen. Springfield KL, Charles Thomas 1976.

Orgill D. Demling RH. Current concepts and approaches in wound healing. Crit Care Med. 1988:16:899–890.

Hunt T. Ehrlich H. Garcia JA et al. Effect of vitamin A on reversing the inhibitory effect of cortisone on healing open wounds in animals and man. Ann surg. 1969:170:633–641.

Bendich A. Carotenoids and immunity. Clin Applied Nutr. 1991:1:45–57.

Ross CA, Temus ME. Vitamin A as a hormone: recent advances in understanding the actions of retinol, retinoic acid and beta carotene. J Amer Diet assoc. 1993:11: 1285–1290.

Bowen PE, Mobaran S. Henderson C. et al. Hypocarotenemia in patients fed enterally with commercial liquid diets. J Parenter Enteral Nutr. 1988: 12:484–489.

Wust B. Beta–carotene in tube feeding. Int J Vit Nutr Res. 1990:60:19–25.

Levenson SM, Demetriou AA, Metabolic factors. In Cohen IK, Diegelmann RF Lindblad WJ. (eds) Wound Healing Biochemical and Clinical Aspects. Philadelphia, PA WB Saunders. 1992.

Reiss E. Pearson E. Art CP, The metabolic response to burns. J Clin Invest. 1956:35:62–77.

Nichols BL, Alvarado J. Hazlewood CR, Viteri F. Magnesium supplementation in protein–calorie malnutrition. Am J Clin Nutr. 1978:31:176–188.

Freeman JB, Wittine MF, Stegink LD, et al. Effects of magnesium infustion on magnesium and nitrogen balance during parenteral nutrition. Can J Surg. 1982:25:570–4.

Pearson E. Soroff HS, Arney GK, et al. An estimation of the potassium requirements for equilibrium in burned patients. Surg. Gynecol Obstet. 1961:112:263–73.

Goodson WH Hunt TK. Wound healing. In Kinney J. Jeejeebhoy K. Hill G. et al. eds. Nutrition and Metabolism in Patient Care. Philadelphia, PA. WB Saunders 1988.

Sanstead H. Lanier V. Shephard G. et al. Zinc and wound healing: effects of zinc deficiency and zinc supplementation. Am J Clin Nutr. 1970:23:514–519.

Pories W. Henzel J. Rob CG. Strain WH. Acceleration of wound healing in man with zinc sulfate given by mouth. Lancet. 1967:121–124.

Hallbook T. Lanner E. Serum zinc and healing of venous leg ulcers. Lancet 1972:780–782.

Bogden G. Oleske JM Lavenhar MA. et al. Zinc and immunocompetence in the elderly; baseline data on zinc nutrition and immunity in unsupplemented subjects. Am J Clin Nutr. 1987:46:101–109.

Bogden JD, Oleske JM, Munves EM, et al. Zinc and immunocompetence in elderly people: effects of zinc supplementation for 3 months. Am J Clin Nutr. 1988:48:655–663.

Prasad AS, Meftah S. Abdallah J et al. Serum thymullin in human zinc deficiency. J Clin Invest 1988:82:1202–1210.

August D. Janghorbani M. Young V. Determination of zinc and copper absorption at three dietary ZN–Cu ratios by using stable isotope methods in young adult and elderly subjects. Am J Clin Nutr. 1989:50:1457–63.

Chandra R. Trace element regulation of immunity and infection. J Amer Coll Nutr. 1985:4:5–16.

Hunt DR, Lane HW, Beesinger D. et al. Selenium depletion in burn patients. J Parenter Enteral Nutr. 1984:8:695–699.

Hayes KC. "Vitamin–like" molecules (D) taurine. In: Shils ME, Yong VR. Modern Nutrition in Health and Disease, 7th ed. Philadelphia: Lea and Febiger 1988:464–470.

Sturmon JA, Hayes KC. The biology of taurine in nutrition and development. Adv. Nutr Res 1980:3:231–299.

Geggel HS, Ament ME, Heckenlively JR, Martin DA, Kopple JD. Nutritional requirement for taurine in patients receiving long–term parenteral nutrition. N Engl J Med 1985:312:142–146.

Vinton NE, Laidlaw SA, Ament ME, Kopple JD. Taurine concentrations in plasma blood cells and urine of children undergoing long–term parenteral nutrition. Pediatr Res 1987:21:399–403.

Borum PR. Role of carnitine in lipid metabolism. In: Honsberger M. Bracco U. Lipids in Modern Nutrition. New York: Raven Press 1987:51–58.

Rudman D. Sewell CW, Ansley JD. Deficiency of carnitine in cachectic cirrhotic patients. J Clin Invest 1977:60:716–723.

Bertoli M. Battistella PA. Vergani L. et al. Carnitine deficiency induced during hemodialysis and hyperlipidemia; effect of replacement therapy. Am J Clin Nutr. 1981:34:1496–1500.

Borum PR, Taggart EM. Carnitine nutriture of dialysis patients. J Am Diet Assoc 1986:86:644–647.

Cederblad G. Larsson J. Nordstrom H. Schildt B. Urinary excretion of carnitine in burned patients. Burns 1981:8:102–109.

Tanphaichitr V. Lerdvuithisopon N. Urinary carnitine excretion in surgical patients on total parenteral nutrition. JPEN 1981:5:505–509.

Cederblad G. Larsson J. Schmidt B. Muscle and plasma carnitine levels and urinary carnitine excretion in multiply injured patients on total parenteral nutrition. Clin Nutr. 1984:2:143–148.

Lapichino G. Radnzzani D. Colombo A. Ronzoni G. Carnitine excretion: a catabolic index of injury. JPEN 1988:12:35–36.

Nanni G. Pittiruti M. Giovannini I. Boldrini G. Ronconi P. Castagneto M. Plasma carnitine levels and urinary carnitine excretion during sepsis. JPEN 1985:9:483–490.

Gibault JP, Frey A. Guiraud M. Schirardin H. Bouletreau P. Bach AC. Effects on L–carnitine infusion on Intralipid clearance and utilization. Study carried out in septic patients on an intensive care unit. J parenter Enteral Nutr 1988:12:29–34.

Borum PR, Nork CM Broquist HP. Carnitine content of liquid formulas and special diets. AM J. Clin Nutr. 1979:32:2272–2276.

Feller AG, Rudman D. Erve PR. et al. Subnormal concentrations of serum selenium and plasma carnitine in chronically tube–fed patients. Am J Clin Nutr. 1987:45:476–483.

Helms RA, Whitinington PF, Maurer EC, et al. enhanced lipid utilization in infants receiving oral L–carnitine during long–term parenteral nutrition. J pediatr. 1986:109:984–988.

Turner FP, Brum VC. The urinary excretion of free taurine in acute and chronic disease following surgical trauma, and in patients with acute alcoholism. J Surg Res. 1964:4:423–431.

Paauw JD, Davis AT, Taurine concentration in serum of critically injured patients and age sex matched health control subjects. Am J Clin Nutr. 1990:52:657–660.

Austin C. Water: guidelines for nutritional support. Nutr. Supp Serv. 1986:6:27–29.

Kubo W. Grant M. Walike B. et al. Fluid and electrolyte problems of tube–fed patients. Am J Nurs 1976:76:912–916.

Wagner D. Nutritional Management of the Pressure Ulcer Patient. On file. Clintec Nutrition Company. 1990.

Dougherty J. Influence of high–protein diets on renal function. J Amer Diet Assoc. 1973:63:392–396.

Stinson J. The importance of water in LTC residents' diets. Contemp Long–term Care. 1987:130–132.

Ross Laboratories Brochure, *Specialized Elemental Nutrition With Glutamine—The Role of Alitraq™ Specialized Elemental Nutrition With Glutamine* (1991).

Ross Laboratories Brochure, *Introducing Alitraq™ Specialized Elemental Nutrition With Glutamine* (1992).

Ross Laboratories Brochure, *Introducing Perative™* (1992).

ENTERAL COMPOSITION FOR MALABSORBING PATIENTS

BACKGROUND OF THE INVENTION

The present invention relates generally to the treatment and nutritional support of patients. More specifically, the present invention relates to compositions for use in malabsorbing patients with elevated protein requirements.

Patients challenged with metabolic stress and injury have a significant need for increased nutrients and energy. Severe injury, trauma and some disease states are associated with loss of the body's nutrient stores. Non-essential nutrients and substances that a body typically can synthesize in adequate supply may become limiting. Additionally, absorption of nutrients from the gut can become compromised even when there is no direct injury to the gastrointestinal system.

Patients suffering from a loss of nutrients require adequate nutritional support. A lack of adequate nutritional support can result in malnutrition associated complications, such as prolonged negative nitrogen balance and depletion of somatic and visceral protein levels. Thus, the goal of nutritional support is to maintain body mass, provide nitrogen and energy in adequate amounts to support healing, meet metabolic demands characterized by the degree of stress, and support immune function.

A traditional form of nutritional support is administering whole protein liquid feedings to the patient to remedy the protein deficiency. However, some patients requiring nutritional support have a compromised absorptive capacity and thus cannot tolerate whole protein liquid feedings. Many diseases or their consequences can cause malabsorption by impairment of either digestion or absorption. For instance, patients suffering from various types of inflammatory bowel diseases typically cannot tolerate whole protein feedings. As a result, semi-elemental and elemental protein diets were developed to treat such compromised patients.

However, in addition to the traditional inflammatory bowel type patients, semi-elemental and elemental protein diets are currently being used in other patient segments. Specific conditions where these diets are being used include, for example, total parenteral nutrition patients receiving early transitional feedings, acutely ill, catabolic patients with increased nitrogen needs yet requiring an elemental diet and critically ill patients not tolerating whole protein liquid tube feedings.

Still further, many patients currently being treated with elemental diets also require elevated protein levels. For instance, patients with Crohn's disease who are experiencing the massive losses of protein associated with protein-losing enteropathy require increased amount of protein. Likewise, patients suffering from diarrhea from hypoalbuminemia, chronic diarrhea with pressure ulcers, and HIV/AIDS related malabsorption and diarrhea require increased protein for adequate nutritional support.

Such malabsorbing patients with increased protein requirements need an elemental diet with elevated nitrogen levels to enhance nutrient absorption, replete protein stores, achieve nitrogen balance and promote anabolism. While a variety of elemental and semi-elemental diets are currently being used in an attempt to treat and/or provide nutritional requirements to such patients, the inventors of the present invention do not believe the needs of such patients are being adequately met.

Accordingly, a need exists for an enteral nutritional formulation that meets the nutrient requirements of malabsorbing patients with elevated protein needs.

SUMMARY OF THE INVENTION

The present invention provides a nutritional composition designed for malabsorbing patients with increased protein needs. To this end, the present invention provides a very high protein, isocaloric, low osmolality, semi-elemental diet with an upgraded lipid and micronutrient profile.

Pursuant to the present invention, the enteral composition includes a protein source constituting approximately 22% to 27% of the caloric distribution of the composition, a carbohydrate source, and a lipid source including a mixture of medium and long chain triglycerides. The composition has an osmolality of approximately 300 to 400 mOsm/kg $H_2O$.

In a preferred embodiment, the protein source is hydrolyzed whey protein.

In another embodiment, the lipid source of the composition includes at least 70% medium chain triglycerides.

In an embodiment, the composition of the present invention has an omega-6 to omega-3 ratio of about to about 8:1.

In yet another embodiment, the composition of the present invention includes a carbohydrate source comprising about 42% to about 45% of the calorie distribution of the composition.

Moreover, in an embodiment, the composition includes an upgraded micronutrient profile. Specifically, the composition includes increased amounts of zinc, vitamin C, taurine, L-carnitine, and selenium. Furthermore, the composition includes a decreased amount of magnesium.

The present invention also provides a method for providing nutrition to malabsorbing patients with elevated protein needs. The method includes administering to the patient an effective amount of a composition including a protein source comprising from approximately 22% to 27% of the caloric distribution of the composition, a carbohydrate source, and a lipid source including a mixture of medium and long chain triglycerides. The composition preferably has an osmolality of approximately 300 to 400 mOsm/kg $H_2O$.

Still further, in another embodiment, the method of the present invention includes the step of administering to a malabsorbing patient an effective amount of a composition comprising a protein source including from approximately 22% to 27% of the caloric distribution of the composition, a carbohydrate source, and a lipid source including a mixture of medium and long chain triglycerides. The composition has an omega-6 to omega-3 fatty acid ratio of approximately 1:1 to 8:1.

An advantage of the present invention is that it provides a nutritional composition that is ready-to-use, nutritionally complete, and contains proteins, lipids, carbohydrates and vitamins and minerals in proportions appropriate for malabsorbing patients with elevated protein needs.

Moreover, an advantage of the present invention is that it provides a nutritional diet for tube and oral use designed for optimal tolerance and absorption in malabsorbing patients.

Another advantage of the present invention is that it provides a composition containing higher levels of key micronutrients so that the product can support the increased requirements of the acutely ill, catabolic patient.

Yet another advantage of the present invention is that it provides malabsorbing patients with a high protein, high MCT and moderate osmolality formula.

Still another advantage of the present invention is that it provides a composition with elevated nitrogen levels to enhance nutrient absorption, replete protein stores, achieve nitrogen balance and promote anabolism.

Additional features and advantages of the present invention are described in, and will be apparent from, the detailed description of the presently preferred embodiments.

DETAILED DESCRIPTION OF THE PRESENTLY PREFERRED EMBODIMENTS

Nutritional support of hospitalized as well as non-hospitalized patients requires prevention, recognition and treatment of nutritional depletion that may occur with illness. The goals of nutritional support include stabilizing metabolic state, maintaining body mass, and/or facilitating growth in the presence of disease and gastrointestinal dysfunction.

Certain disease states exist that alter intake, absorption or metabolism. For example, certain health conditions can impair the nutrient absorption and/or reduce gastrointestinal tolerance for diets which are based on whole proteins. These conditions include patients suffering specifically from a compromised gut function as well as patients, due to the severity of their condition, who are simply unable to tolerate whole protein diets. For purposes of the present application, this population of patients are generically referred to as malabsorbing patients.

The present invention provides a product that is specifically directed to meet the metabolic needs of patients suffering from a malabsorbing condition. More specifically, the present invention provides a product designed for malabsorbing patients with increased protein needs. To this end, the present invention provides a high protein, high medium chain triglyceride product with increased levels of key micronutrients.

The protein source of the present invention provides approximately 22 to 27% of the total calories of the composition. In an embodiment, the protein source comprises approximately 25% of the total calories of the composition. This high protein concentration is designed to provide sufficient protein to replete lean body mass in patients with elevated protein losses. Elevated protein requirements have been identified in patient populations such as pressure ulcer, serious wounds, trauma, Crohn's disease with protein-losing enteropathy, chronic diarrhea, and HIV/AIDS malabsorption and diarrhea. Inherent to the metabolic requirements of these conditions is an increased loss of nitrogen, increased requirement for protein or both.

The composition of the present invention is a peptide-based diet. In choosing the protein source, the present invention maximizes tolerance and absorption with the use of a hydrolyzed protein. In a preferred embodiment, the protein source is enzymatically hydrolyzed whey protein. This type of protein source reduces the incidence of gastric reflux because gastric emptying is faster than with diets containing casein or whole whey. Also, hydrolyzed whey protein serves as a rich source of the amino acid cysteine, which is a limiting amino acid for the formation of glutathione.

Carbohydrates provide, in an embodiment, approximately 35% to 50% and, most preferably, approximately 42% to 45% of the caloric content of the composition. In an embodiment, the carbohydrate source is approximately 42% of the caloric content of the composition. A number of carbohydrates can be used, pursuant to the present invention, including maltodextrin.

The lipid source of the present invention includes a mixture of medium chain triglycerides (MCT) and long chain triglycerides (LCT). The lipid source of the present invention is approximately 25% to about 40% of the caloric content of the composition. In an embodiment, the lipid source is approximately 33% of the caloric content of the composition.

The lipid profile is designed to meet essential fatty acid needs (omega-3 and omega-6) while also keeping MCT content high and LCT content low compared with prior formulas. The lipid source of the present invention includes at least 70% from medium chain triglycerides. Such medium chain triglycerides are easily absorbed and metabolized in the acutely ill, catabolic patient. In a preferred embodiment, the medium chain triglyceride source is fractionated coconut oil.

The remainder of the lipid source is a mixture of long chain triglycerides. Suitable sources of long chain triglycerides are canola oil, corn oil, soy lecithin and residual milk fat. The lipid profiles containing such long chain triglycerides is designed to have a polyunsaturated fatty acid omega-6 (n-6) to omega-3 (n-3) ratio of approximately 1:1 to 8:1. The proposed ratio of n-6:n-3 is designed to reduce the immune suppression associated with high omega-6 fatty acid concentration and provide adequate essential fatty acid. In an embodiment, the composition includes an omega-6 to omega-3 ratio of 7.7:1.

In addition to the requirements for high protein as a percentage of total calories, malabsorbing patients may also have elevated requirements of certain vitamins and minerals, and trace elements. To this end, the present invention also includes a specialized vitamin and mineral profile. The enhanced vitamin and mineral profile is designed to support patients with elevated healing needs, such as acutely ill, catabolic patients.

Pursuant to the present invention, the composition includes a high level of zinc. Preferably, at least approximately 150% of the USRDA of zinc is provided in the composition per 1000 Kcal. In an embodiment, 19 to 29 mg per 1000 calories of zinc are provided. In a preferred embodiment, 24 mg per 1000 calories of zinc is provided. The increased zinc compensates for zinc losses and provides increased zinc for tissue repair in a patient having increased healing requirements.

The composition of the present invention also includes an increased amount of vitamin C. At least approximately 500% of the USRDA of vitamin C is provided per 1000 Kcal. In an embodiment, 270 to 410 mg per 1000 calories of vitamin C is provided. In a preferred embodiment, 340 mg per 1000 calories of vitamin C is provided. Vitamin C is believed to accelerate the healing and granulation in patients with severe healing requirements. Vitamin C will support increased requirements/losses after surgery.

Pursuant to the present invention, the composition also includes increased amounts of selenium. Selenium deficiencies may develop in patients having elevated healing requirements. Pursuant to the present invention, at least approximately 40 to 60 mg of selenium are provided in 1000 calories of formula. In a preferred embodiment, approximately 50 mg of selenium per 1000 calories is provided.

Many of the commercially available enteral formulas contain far below the amount of carotenoids (beta-carotene) found in the usual diets of normal healthy people. In fact, patients on liquid formula diets as their sole source of nutrition for one week or more have been found to have plasma concentrations of carotenoids of only 8 to 18% as compared to controls consuming a free choice diet. See Bowen et al, *Hypocarotenemia in patients Fed Enterally With Commercial Liquid Diets*, JPEN, 12(5):44–49 (1988). Those on enteral formulas for more than three weeks have negligible concentrations of any common serum carotenoids.

To meet these requirements, the present invention includes a source of beta-carotene. Beta-carotene is added to the composition to normalize beta-carotene serum plasma levels and avoid beta-carotene deficiency in long term tube-fed patients. The composition preferably includes approximately 1.6 to 2.4 mg per 1000 calories. This amount prevents deficiencies and provides for possible increased requirements in the healing patient. Moreover, the beta-carotene levels allow plasma concentrations to be increased to near normal optimal levels of 500 mcg per liter.

The present invention also provides increased amounts of L-carnitine and taurine to support the increased requirements of the acutely ill, catabolic patient. Both taurine and L-carnitine are preferably present in amounts of approximately 80 to 120 mg per 1000 calories. In preferred embodiments, both taurine and L-carnitine are present in an amount of approximately 100 mg per 1000 calories.

Still further, the composition of the present invention includes decreased amounts of magnesium. Magnesium has been associated with diarrhea. In an embodiment, magnesium is present in an amount of approximately 237 mg to 355 mg per 1000 calories. In a preferred embodiment, magnesium is present in an amount of approximately 300 mg per 1000 calories.

The composition of the present invention is a ready-to-use enteral formulation. The composition can be used as a supplement or for total enteral nutritional support. The composition can be tube-fed to a patient, or fed by having the patient drink same. Preferably, the caloric density of the composition is 1.0 kcal/ml. Furthermore, unlike prior formulations, the composition of the present invention has a low osmolality of approximately 300 to 400 mOsm/kg $H_2O$ in an unflavored product. The osmolality of the composition in a flavored product is approximately 350 to 450 mOsm/kg $H_2O$.

The composition of the present invention may be utilized to treat malabsorbing patients. As used herein, malabsorbing patients are patients who, due to either a disorder or condition, are unable to tolerate whole protein diets. For example, the present invention may be utilized to provide nutrition to critically ill patients transitioning from total parenteral nutrition therapy and acutely ill, catabolic patients with increased nitrogen needs. Moreover, the present invention can be utilized to provide nutrition to patients suffering from the following conditions and/or diseases: trauma; pressure ulcers; cancer; infectious disease; HIV/AIDS; and Crohn's disease.

Typically, on average, approximately 2000 Kcal of composition will be given per day to a malabsorbing patient. Of course, some patients with very high requirements may require substantially more composition and some patients with lower requirements, and/or weights, may require less composition. For instance, a malabsorbing patient with substantially elevated protein requirements will require more composition than a patient not requiring increased amounts of protein.

By way of example, and not limitation, an example of a suitable composition that may be used pursuant to the present invention is as follows.

The composition includes the following ingredients: water; maltodextrin, enzymatically hydrolyzed whey protein, medium-chain triglycerides (MCT source: fractionated coconut oil); corn starch; soy bean oil; soy lecithin; potassium phosphate; guar gum; calcium citrate; sodium phosphate; choline chloride; sodium chloride; calcium phosphate; calcium ascorbate; magnesium chloride; potassium citrate; magnesium oxide; potassium chloride; taurine; citric acid; L-carnitine; zinc sulfate; ferrous sulfate; DL-alpha tocopherylacetate; nicotinamide; retinyl palmitate; calcium pantothenate; manganese sulfate; copper sulfate; pyridoxine hydrochloride; riboflavin; thiamine; folic acid; cholecal ciferol; biotin; potassium iodide; beta carotene; sodium molybdate; chromium chloride; phylloquinone; sodium selenate; and cyanocobalamin.

The composition of the present invention has the following nutrient composition (per 1000 calories):

| Nutrient Composition | Amount | % U.S. RDA* |
|---|---|---|
| Protein | 62.5 g | 139 |
| Carbohydrate | 104.5 g | ** |
| Fat*** | 39 g | ** |
| Water | 841 ml | ** |
| Vitamin A | 7332 IU**** | 147 |
| Vitamin D | 400 IU | 100 |
| Vitamin E | 30 IU | 100 |
| Vitamin K | 80 mcg | ** |
| Vitamin C | 340 mg | 567 |
| Thiamine ($B_1$) | 2 mg | 133 |
| Riboflavin ($B_2$) | 2.4 mg | 141 |
| Niacin | 28 mg | 140 |
| Vitamin $B_6$ | 4 mg | 200 |
| Folic Acid | 540 mcg | 135 |
| Pantoth. Acid | 14 mg | 140 |
| Vitamin $B_{12}$ | 8 mcg | 133 |
| Biotin | 400 mcg | 133 |
| Choline | 450 mg | ** |
| Taurine | 100 mg | ** |
| L-Carnitine | 100 mg | ** |
| Calcium | 800 mg | 80 |
| Phosphorus | 700 mg | 70 |
| Magnesium | 300 mg | 75 |
| Zinc | 24 mg | 160 |
| Iron | 18 mg | 100 |
| Copper | 2 mg | 100 |
| Magnesium | 2.7 mg | ** |
| Iodine | 150 mcg | 100 |
| Sodium | 560 mg | ** |
| Potassium | 1500 mg | ** |
| Chloride | 1000 mg | ** |
| Chromium | 40 mcg | ** |
| Molybdenum | 120 mcg | ** |
| Selenium | 50 mcg | ** |

*U.S. Recommended Daily Allowance for Adults and Children 4 or More Years of Age
**U.S. RDA Not Established.
***MCT Provides 27 Grams Per 1000 ml
****Includes 2 mg from Beta-Carotene It will be understood that various modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. An enteral composition designed for malabsorbing patients comprising:

a single protein source consisting essentially of hydrolyzed whey protein that comprises from approximately 22% to 27% of the caloric distribution of the composition;

a carbohydrate source; and a lipid source including a mixture of medium and long chain triglycerides.

2. The enteral composition of claim 1 wherein the composition has an osmolality of approximately 300 to 450 mOsm/Kg $H_2O$.

3. The enteral composition of claim 1 wherein the lipid source includes at least 70% medium chain triglycerides.

4. The enteral composition of claim 1 wherein the composition has an omega-6 to omega-3 ratio of about 1:1 to about 8:1.

5. The enteral composition of claim 1 including approximately 300 mg of magnesium per 1000 Kcal of composition.

6. The enteral composition of claim 1 wherein the composition includes per 1000 Kcal of composition:
- a zinc source providing from approximately 19 to 29 mg;
- a vitamin C source providing from approximately 270 to 410 mg;
- a selenium source providing from approximately 40 to 60 mg;
- a taurine source providing from approximately 80 to 120 mg; and
- a L-carnitine source providing from approximately 80 to 120 mg.

7. The enteral composition of claim 1 wherein the composition includes a source of beta carotene.

8. A method for providing nutrition to a malabsorbing patient comprising administering to the patient an effective amount of a composition comprising:
- a single peptide based protein source consisting essentially of hydrolyzed whey comprising approximately 22% to 27% of the caloric distribution of the composition;
- a carbohydrate source; and
- a lipid source including a mixture of medium and long chain triglycerides, the composition having an osmolality of approximately 300 to 400 mOsm/Kg.

9. The method of claim 1 wherein the lipid source includes at least 70% medium chain triglycerides.

10. The method of claim 8 wherein the composition has an omega-6 to omega-3 ratio of about 1:1 to about 8:1.

11. The method of claim 8 wherein the composition includes per 1000 Kcal of composition:
- a zinc source providing from approximately 19 to 29 mg;
- a vitamin C source providing from approximately 270 to 410 mg;
- a selenium source providing from approximately 40 to 60 mg;
- a taurine source providing from approximately 80 to 120 mg; and
- a L-carnitine source providing from approximately 80 to 120 mg.

12. The method of claim 8 wherein the malabsorbing patient suffers from a gastrointestinal disorder.

13. The method of claim 8 wherein the malabsorbing patient is a moderately catabolic patient.

14. A method for providing nutrition to malabsorbing patient comprising administering to the patient an effective amount of a composition comprising:
- a single peptide based protein source consisting essentially of whey hydrolysate and comprising approximately 22% to 27% of the caloric distribution of the composition;
- a carbohydrate source; and
- a lipid source including a mixture of medium and long chain triglycerides, the composition having an omega-6 to omega-3 fatty acid ratio of approximately 1:1 to 8:1.

15. The method of claim 14 wherein the lipid source includes at least 70% medium chain triglycerides.

16. The method of claim 14 wherein the composition has an osmolality of approximately 300 to 400 mOsm/Kg.

17. The method of claim 14 wherein the composition includes per 1000 Kcal of composition:
- a zinc source providing from approximately 19 to 29 mg;
- a vitamin C source providing from approximately 270 to 410 mg;
- a selenium source providing from approximately 40 to 60 mg;
- a taurine source providing from approximately 80 to 120 mg; and
- a L-carnitine source providing from approximately 80 to 120 mg.

18. The method of claim 14 wherein the composition includes a source of beta-carotene.

19. An enteral composition designed for malabsorbing patients comprising:
- a single protein source consisting essentially of hydrolyzed whey protein that comprises from approximately 22% to about 27% of the caloric distribution of the composition;
- a carbohydrate source; and
- a lipid source including a mixture of medium and long chain triglycerides the medium chain triglycerides comprising at least 70% of the caloric content of the lipid source.

20. The enteral composition of claim 19 wherein the composition has an osmolality of approximately 300 to about 450 mOsm/Kg H$_2$O.

21. The enteral composition of claim 19 including approximately 300 mg of magnesium per 1000 Kcal of composition.

22. The enteral composition of claim 19 wherein the composition includes per 1000 Kcal of composition:
- a zinc source providing from approximately 19 to about 29 mg;
- a vitamin C source providing from approximately 270 to about 410 mg;
- a selenium source providing from approximately 40 to about 60 mg;
- a taurine source providing from approximately 80 to about 120 mg; and
- a L-carnitine source providing from approximately 80 to about 120 mg.

23. An enteral composition designed for malabsorbing patients comprising:
- a single protein source consisting essentially of hydrolyzed whey protein that comprises from approximately 22% to about 27% of the caloric distribution of the composition;
- a carbohydrate source; and
- a lipid source including a mixture of medium and long chain triglycerides, the medium chain triglycerides comprising at least 70% of the caloric content of the lipid source and the lipid source having an omega-6 to omega-3 ratio of not more than 8:1.

24. The enteral composition of claim 23 wherein the composition has an osmolality of approximately 300 to about 450 mOsm/Kg H$_2$O.

25. The enteral composition of claim 23 including approximately 300 mg of magnesium per 1000 Kcal of composition.

26. The enteral composition of claim 23 wherein the composition includes per 1000 Kcal of composition:
- a zinc source providing from approximately 19 to about 29 mg;

a vitamin C source providing from approximately 270 to about 410 mg;

a selenium source providing from approximately 40 to about 60 mg;

a taurine source providing from approximately 80 to about 120 mg; and a L-carnitine source providing from approximately 80 to about 120 mg.

27. The enteral composition of claim 23 wherein the composition includes a source of beta carotene.

28. A method for providing nutrition to a malabsorbing patient comprising administering to the patient an effective amount of a composition comprising:

a single peptide based protein source consisting essentially of hydrolyzed whey comprising approximately 22% to about 27% of the caloric distribution of the composition;

a carbohydrate source; and a lipid source including a mixture of medium and long chain triglycerides, wherein the medium chain triglycerides comprise at least 70% of the lipid source.

29. The method of claim 28 wherein the composition has an omega-6 to omega-3 ratio of about 1:1 to about 8:1.

30. The method of claim 28 wherein the composition includes per 1000 Kcal of composition:

a zinc source providing from approximately 19 to about 29 mg;

a vitamin C source providing from approximately 270 to about 410 mg;

a selenium source providing from approximately 40 to about 60 mg;

a taurine source providing from approximately 80 to about 120 mg; and a L-carnitine source providing from approximately 80 to about 120 mg.

31. The method of claim 28 wherein the malabsorbing patient suffers from a gastrointestinal disorder.

32. The method of claim 28 wherein the malabsorbing patient is a moderately catabolic patient.

33. A method for providing nutrition to a malabsorbing patient requiring glutathione repletion comprising administering to the patient an effective amount of a composition comprising:

a single protein source consisting essentially of hydrolyzed whey;

a carbohydrate source; and a lipid source including a mixture of medium and long chain triglycerides.

34. The method of claim 33 wherein the lipid source includes at least 70% medium chain triglycerides.

35. The method of claim 33 wherein the composition has an omega-6 to omega-3 ratio of about 1:1 to about 8:1.

36. The method of claim 33 wherein the composition includes per 1000 Kcal of composition:

a zinc source providing from approximately 19 to about 29 mg;

a vitamin C source providing from approximately 270 to about 410 mg;

a selenium source providing from approximately 40 to about 60 mg;

a taurine source providing from approximately 80 to about 120 mg; and a L-carnitine source providing from approximately 80 to about 120 mg.

* * * * *